(12) United States Patent
Dewald et al.

(10) Patent No.: US 6,657,110 B1
(45) Date of Patent: Dec. 2, 2003

(54) CYTOPLASM FOR MAIZE

(75) Inventors: Chester L. Dewald, Woodward, OK (US); Phillip L. Sims, Woodward, OK (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 09/377,513

(22) Filed: Aug. 19, 1999

Related U.S. Application Data

(63) Continuation of application No. 09/247,764, filed on Feb. 9, 1999, now abandoned.

(51) Int. Cl.$^7$ .............................. A01H 1/00; A01H 5/00; A01H 5/10; C12N 5/04
(52) U.S. Cl. .................... 800/320.1; 800/269; 800/275; 435/412; 435/424; 435/430; 435/430.1
(58) Field of Search ................................ 435/410, 424, 435/430, 430.1, 412; 800/260, 269, 295, 320.1, 275

(56) References Cited

U.S. PATENT DOCUMENTS 5,330,547 A * 7/1994 Eubanks et al. ............... 47/58

OTHER PUBLICATIONS

Eubanks et al. 1995. A cross between two maize relatives; *Tripsacum dactuloides* and *Zea diploperenis*. Economic Botany 49(2):172–182.*

Eubanks et al. 1997. Molecular analysis of crosses between *Tripsacum dactyloides* and *Zea diploperennis*. Theor. Appl. Genet. 94:707–712.*

Viands et al. 1988. Chapter 30, Pollination control: mechanical and sterility. pp 931–960, In: Alfalfa and alfalfa improvement, Agronomy Monograph No. 29, Crop Sci. Soc. of America, Madison, WI.*

Galinat et al . 1977. The origin of corn. Pp. 27–39, In: Corn and corn improvement. Agronomy Monograph No. 18. Ed. G.F. Sprague, American Soc. Of Agronomy, Madison, WI.*

* cited by examiner

*Primary Examiner*—David T. Fox
(74) *Attorney, Agent, or Firm*—John D. Fado; Randall E. Deck

(57) ABSTRACT

Novel maize plants having a nuclear genome of maize chromosomes with no Tripsacum chromosomes, but with extranuclear genes or cytoplasmic DNA from *Tripsacum floridanum* are disclosed. These novel maize plants are fertile and may be readily crossed as the female parent with any maize as the male line, and the progeny thereof will retain the Tripsacum extranuclear genes. The maize plants may be used to convey the Tripsacum extranuclear genes into any maize breeding or inbred line, or to produce novel maize hybrids or inbred lines possessing the Tripsacum extranuclear genes. Maize plants having the Tripsacum extranuclear genes will exhibit modified traits which are controlled by the extranuclear genes or influenced by the interaction of the extranuclear genes with the maize nuclear genome, including one or more of increased disease and insect resistance, particularly increased resistance to the corn rootworm complex, and the production of aerenchyma in the roots.

27 Claims, No Drawings

CYTOPLASM FOR MAIZE

CROSS-REFERENCE TO RELATED CASES

This application is a continuation of Ser. No. 09/247,764 filed on Feb. 9, 1999, now abandoned the contents of which are incorporated by reference herein.

BACKGROUND OF THE INVENTION

1. Field of the Invention

This invention relates to a novel maize plant having a nuclear genome of maize chromosomes, and an extranuclear genome of *Tripsacum floridanum* extranuclear genes.

2. Description of the Prior Art

Each year, an estimated 71 million acres of maize are planted in the seventeen major corn producing states of the U.S. alone, as reported by the National Agricultural Pesticide Impact Assessment Program (NAPIAP) (Biologic and Economic Assessment of Pesticide Use on Corn and Soybeans, NAPIAP Report No. 1-CA-95). The principal use of field maize is for livestock feed (60%). Significant amounts of the maize crop are also used for human consumption as sweet maize, sweeteners, cooking oil, margarine, processed meal, starches, and syrups, and for the production of ethanol.

Scientists have traditionally used cross-breeding and hybridization techniques to produce maize plants having desirable traits such as increased yields, resistance to disease and pests, increased hardiness, improved nutritional value, and taste.

Breeding programs have also included attempts to cross maize or its wild relatives with perennial gama grass, *Tripsacum dactyloides*. Kindiger and Sokolov (U.S. Pat. No. 5,710,367) disclosed the production of apomictic maize and apomictic maize/Tripsacum hybrids. These apomictic plants, which reproduce asexually, were produced by intercrossing maize (*Zea mays*) with the above-mentioned *Tripsacum dactyloides*. Eubanks (U.S. Pat. No. 5,750,828) has also disclosed the production of a new species, designated Tripsacorn, produced by crossing two perennials, *Zea diploperennis* with *Tripsacum dactyloides*. Tripsacorn is disclosed as being a fertile perennial having a diploid chromosome number between 18 and 20, and which is cross-fertile with maize.

SUMMARY OF THE INVENTION

We have now discovered novel maize plants having a nuclear genome of maize chromosomes with no Tripsacum chromosomes, but with extranuclear genes or cytoplasmic DNA from *Tripsacum floridanum*. These novel maize plants are fertile and may be readily crossed as the female parent with any maize (as the male parent) and the progeny thereof will retain the Tripsacum extranuclear genes. Moreover, by using an inbred maize line as the male parent in such a cross, followed by repeatedly backcrossing the progeny thereof as the female parent with the same inbred line, the inbred line may be placed in a, *Tripsacum floridanum* cytoplasm. In other words, the resultant inbred maize will possess a nuclear genome substantially identical to the parent inbred maize line but it will have the extranuclear genes of *Tripsacum floridanum* rather than those of the parent maize.

Maize plants having these Tripsacum extranuclear genes will exhibit modified traits which are controlled by the extranuclear genes or influenced by the interaction of the extranuclear genes with the maize nuclear genome. Traits which may be exhibited include one or more of increased disease and insect resistance, particularly increased resistance to the corn rootworm complex, and the production of aerenchyma in the roots.

In accordance with this discovery, it is an object of this invention to provide maize plants having a nuclear genome of maize chromosomes with no Tripsacum chromosomes, but with the extranuclear genes of *Tripsacum floridanum*.

Another object of this invention is to provide maize plants and methods which may be used to transfer the extranuclear genes of *Tripsacum floridanum* into any maize line.

It is also an object of this invention to provide maize plants which exhibit increased disease and insect resistance, and/or the production of aerenchyma in the roots.

Still another object of this invention is to provide maize plants which may be used to restore male fertility in maize lines.

Other objects and advantages of this invention will become readily apparent from the ensuing description.

DETAILED DESCRIPTION OF THE INVENTION

In producing the maize plants of this invention we have conveyed the extranuclear genes of *Tripsacum floridanum* into maize without introducing any Tripsacum chromosomes or nuclear DNA into the maize nuclear genome. Thus, the nuclear genome of this maize retains a full complement of maize chromosomes (2n=20 or 20+) with no Tripsacum chromosomes, while its extranuclear genes are from *Tripsacum floridanum*, not maize. As used herein, extranuclear genes, which are also referred to as the plasma genes or the cytoplasmic genome or genes, include the organelle genome, specifically the genomes of the mitochondria and chloroplast.

Because the maize plants of this invention possess a nuclear genome of only maize chromosomes, they resemble normal maize in appearance and growth, including but not limited to properties such as chromosome number, plant height, ear height, no. of ears per stalk, ear size, no. of kernel rows per ear, kernel color, size, weight, and shape, and leaf blade properties such as size and color. The precise characteristics of the maize will of course vary with its parent maize lines, with expressed traits generally being derived from each parent.

Although the maize plants having the Tripsacum extranuclear genes appear as normal maize, they will nonetheless exhibit modified traits which are controlled by the extranuclear genes or influenced by the interaction of the extranuclear genes with the maize nuclear genome. For instance, without being limited thereto, traits which may be exhibited include one or more of the following: increased disease and insect resistance, particularly increased resistance to the corn rootworm complex, better developed and substantially increased numbers of aerenchyma in the roots.

The maize of this invention, which may also be considered a maize cybrid, were produced by first crossing two Tripsacum species to produce an interspecific hybrid. The interspecific hybrid was then hybridized with different maize lines (*Zea mays*) in a series of crosses to transfer the extranuclear genes of the Tripsacum into the maize. The progeny from each cross were selected which exhibited successively reduced numbers of Tripsacum chromosomes, eventually producing a maize plant which possessed a nuclear genome comprising maize chromosomes with no Tripsacum chromosomes, but which retained the Tripsacum extranuclear genes. With each cross it was necessary to use the plants containing the Tripsacum extranuclear genes as the female parent, because the extranuclear genes of these plants always convey with the female parent during sexual reproduction.

As described in greater detail in Example 1, a first cross was made between two Tripsacum species, *T. floridanum* as the female parent and *T. dactyloides* as the male parent, to produce an interspecific hybrid having *T. floridanum* extranuclear genes. This interspecific hybrid was then crossed as a female parent with a first maize line as a male parent to produce an $F_1$ hybrid having a nuclear genome composed of a combination of maize chromosomes and Tripsacum chromosomes, and having the *T. floridanum* extranuclear genes. The resultant $F_1$ hybrid was then crossed as a female parent with a second maize line as a male parent to produce a second hybrid, referred to as $BC_1$, with a nuclear genome having a full complement of maize chromosomes in combination with Tripsacum chromosomes, while retaining the extranuclear genes from the Tripsacum parent. $BC_1$ was crossed as a female parent with a third maize line, producing a third hybrid, $BC_2$, having a nuclear genome of maize chromosomes and a variable, reduced number of Tripsacum chromosomes, with the Tripsacum extranuclear genes. $BC_2$ plants having lowest numbers of Tripsacum chromosomes were selected and crossed with a fourth maize line, producing a fourth hybrid, $BC_3$, all of which retained the Tripsacum extranuclear genes, with further reduced numbers of Tripsacum chromosomes in the nuclear genome. Some members of the $BC_3$ generation possessed no Tripsacum chromosomes, and those individuals were selected and selfed, producing progeny, referred to as $BC_4$, with a nuclear genome having a full complement of maize chromosomes only, with the extranuclear genes of *Tripsacum floridanum*. None of the plants within the $BC_4$ generation were found to possess any Tripsacum chromosomes. Maize plants of the $BC_4$ generation were selfed, producing the $BC_5$ generation, which possessed a nuclear genome of only maize chromosomes with no chromosomes of Tripsacum, and the extranuclear genes of *Tripsacum floridanum*.

Plants of the $BC_4$ and $BC_5$ generations appear as typical maize. Because the $BC_4$ and $BC_5$ were produced from crosses involving four different parent maize lines, they are not inbred lines and individual plants within each generation will be somewhat segregating for different characteristics. However, all plants have the appearance of maize, including the properties described above. Furthermore, the protein, carbohydrate, and oil contents are all comparable to maize, although the oleic oil content is surprisingly high. The karyotype of the $BC_4$ generation consists of 20 complete maize chromosomes plus 1 maize chromosome telomer, the telomer being inherited from a GS-1 ig maintainer white maize line [Kindiger, B. and Hamann, S., 1993, "Generation of haploids in maize: a modification of the indeterminate gametophyte (ig) system", Crop Science, 33(2):342–344], the contents of which are incorporated by reference herein] which was used in the cross with the $BC_2$ hybrid and is a tertiary trisomic (i.e., TB-3Ld(Ig)). In contrast, the karyotype of the $BC_5$ generation includes the 20 complete maize chromosomes, with approximately three-fourths of individual plants possessing the same telomer, and the remaining one-fourth of the plants lacking this component.

Unlike their male parents however, the plants of the $BC_4$ and $BC_5$ generations do exhibit certain traits which appear to be attributable to the Tripsacum extranuclear genes. For example, these plants possess significantly increased numbers of and better developed aerenchyma in their roots. It is envisioned that the presence of aerenchyma in the roots will enhance the ability of the plants to grow in diverse soil conditions, allowing the plant roots to penetrate compact soils, as well as allowing the plants to grow in water-logged soils. Another property that the plants are expected to exhibit includes, but is not limited to, increased resistance to disease and insect pests, particularly to the corn rootworm complex.

Maize plants possessing the Tripsacum extranuclear genes may be stably maintained by conventional selfing or breeding as described hereinbelow, provided that a maize plant possessing the Tripsacum extranuclear genes is used as the female parent.

A sample of at least 2,500 seeds from the $BC_4$ generation plants, which possess a nuclear genome of either 20 or 20+ chromosomes of *Zea mays* with no chromosomes of Tripsacum, and which also possess the extranuclear genes of *Tripsacum floridanum*, has been deposited under the conditions of the Budapest. Treaty with the American Type Culture Collection (10801 University Blvd, Manassas, Va., 20110–2209, USA) on Jan. 29, 1999, and has been assigned deposit accession no. ATCC 203622.

In the preferred embodiment, the maize plants of this invention are used for producing maize plants by crossing as a female parent with a second maize plant (*Zea mays*) as the male parent. This second parent maize may be the same as or different from the first parent. Thus, any such methods of using maize having a nuclear genome of maize chromosomes with no Tripsacum chromosomes, but with extranuclear genes of *Tripsacum floridanum*, are encompassed herein, including but not limited to selfing, backcrossing, inbred production, hybrid production, and crosses to populations. This can be practiced with any type of maize, including but not limited to dents, flints, popcorn, and sweet corn. In a particularly preferred embodiment, the maize plants are used in a conventional maize breeding program in order to incorporate the Tripsacum extranuclear genes into other different maize lines or varieties to produce inbred or breeding lines or hybrids having superior characteristics as well as the improved properties conveyed by the Tripsacum extranuclear genes.

Preferred breeding programs will typically employ well-known techniques. By way of illustration, breeding techniques which are suitable for use herein include but are not limited to those described by Hallauer et al. (Corn and Corn Improvement, 3rd ed., Agronomy Soc. America, 1988, pp. 469–564, the contents of which are incorporated by reference herein). However, because the extranuclear genes always convey with the female parent when crossed, it is essential that in order to transfer the Tripsacum extranuclear genes to another maize line or variety, the plants containing the Tripsacum extranuclear genes must always be used as the female parent or seed line in each cross. The maize line or variety into which it is desired to transfer the Tripsacum extranuclear genes must therefore be used as the male parent or pollen line in any cross.

In one particularly preferred embodiment, the transfer of the Tripsacum extranuclear genes will be typically performed by crossing the maize plant of this invention as the female parent to a normal elite inbred line. As expected, the progeny from this cross will segregate with respect to traits effected by the maize, chromosomal DNA, but all progeny will possess the Tripsacum extranuclear genes. The plants that possess the desired traits may then be crossed again as the female parent to the normal plant line resulting in progeny which segregate once more. As before however, all progeny will retain the Tripsacum extranuclear genes. This backcrossing process is repeated, always using the progeny containing the Tripsacum extranuclear genes as the female parent, until the recurrent parent has been converted to a line containing the Tripsacum extranuclear genes and also possessing all other important attributes originally found in the recurrent parent. This typically require about 6–8 generations.

Another aspect of this invention is to provide for cells which upon growth and differentiation produce maize plants which possess a nuclear genome of only maize chromosomes with no chromosomes of Tripsacum, and the extranuclear genes of *Tripsacum floridanum*. Thus, as used herein, the term "maize plant or parts thereof" includes plant cells, plant protoplasts, plant cells of tissue culture from which maize plants can be regenerated, plant calli, plant clumps, and plant cells that are intact in plants or parts of plants such as, flowers, embryos, ovules, roots, root tips, kernels, ears, cobs, silk, pollen sacks, leaves, husks, stalks, and the like.

Techniques for the tissue culture of maize with a high rate of success have been previously described and are suitable for use herein. See Gogerty (U.S. Pat. No. 5,841,015) the contents of which are incorporated by reference herein. Illustrative examples of tissue culture techniques which may be used include but are not limited to those described by European Patent Application publication 160,390, Green and Rhodes ("Plant Regeneration in Tissue Culture of Maize", Maize for Biological Research, Plant Molecular Biology Association, Charlottesville, Va., 1982, pp. 367–372), Duncan et al. (1985, "The Production of Callus Capable of Plant Regeneration from Immature Embryos of Numerous *Zea Mays* Genotypes," Planta, 165:322–332, 1985), Songstad et al. (1988, Plant Cell Reports, 7:262–265), Rao et al., (1986, Maize Genetics Cooperation Newsletter, 60:64–65), and Conger et al., (1987, Plant Cell Reports, 6:345–347), the contents of each of which are incorporated by reference herein.

In accordance with this invention, either or both of the nuclear maize DNA and the Tripsacum extranuclear genes may be modified using conventional techniques. Thus, the terms "maize chromosomes" and "*Tripsacum floridanum* extranuclear genes" used herein include not only native or naturally occurring maize chromosomes and *T. floridanum* extranuclear genes, respectively, but also maize chromosomes and *T. floridanum* extranuclear genes which have been modified to include heterologous genes and/or mutations therein. For example, transformation techniques which may be used herein include: microparticle gene transfer such as described by Lowe et al. (1995, Bio/Technology, 13:677–682), pollen transformation techniques such as described by Ohta (1986, Proc. Nat'l Acad. Sci. USA, 83:715–719), Smith et al. (1994, Plant Science, 104:49–58), and dewet (International Patent Application WO 85/01856), electroporation techniques such as described by Rhodes (1988, Science, 240:204–207), Krzyzk et al. (U.S. Pat. No. 5,384,253), and viral transformation such as described by Langenberg et, al. (U.S. Pat. No. 5,416,010). Techniques for introducing mutations include conventional chemical or irradiation techniques for random mutagenesis, or insertional or site directed point mutagenesis processes such as described by Neufer ["Induction of Genetic Variability", In: Maize Breeding and Genetics, Walden (ed.), 1978, pp. 579–600]. It is understood that the techniques for transformation and mutation are not limited to the maize nuclear genome but may be used to modify the Tripsacum extranuclear genes, including the chloroplast or mitochondrial DNA, as well. The contents of each of the above-mentioned references are incorporated by reference herein.

The maize plants of this invention may be used for the production of livestock feed, for human consumption as sweet maize, popcorn, sweeteners, cooking oil, margarine, processed meal, starches, and syrups, and for the production of ethanol and other industrial products which are conventional in the art.

The following examples are intended only to further illustrate the invention and are not intended to limit the scope of the invention which is defined by the claims.

EXAMPLE 1

Maize which possess a nuclear genome of only maize chromosomes with no chromosomes of Tripsacum, and the extranuclear genes of *Tripsacum floridanum* were prepared from crosses of two Tripsacum species followed by hybridization with four different common maize lines in a series of crosses. The pedigree of the hybrids so produced is summarized as follows:

| Cross | Female parent | Male parent | Progeny |
|---|---|---|---|
| 1 | T. floridanum | T. dactyloides | interspecific Tripsacum |
| 2 | interspecific Tripsacum | supergold popcorn | $F_1$ intergeneric |
| 3 | $F_1$ intergeneric | BK-16 purple tester maize | $BC_1$ |
| 4 | $BC_1$ | yellow inbred maize | $BC_2$ |
| 5 | $BC_2$ | GS*1 ig maintainer white maize | $BC_3$ |
| 6 | $BC_3$ | $BC_3$ | $BC_4$ |
| 7 | $BC_4$ | $BC_4$ | $BC_5$ |

The progeny of each cross were examined to determine karyotype and male fertility. In review, the first cross was made between two Tripsacum species, *T. floridanum* as the female parent and *T. dactyloides* as the male parent, to produce an interspecific hybrid having *T. floridanum* extranuclear genes and nuclear genes of both *T. floridanum* and *T. dactyloides*. This interspecific hybrid was then crossed as a female parent with a first maize line as a male parent to produce an $F_1$ hybrid having a nuclear genome composed of a combination of maize chromosomes and Tripsacum chromosomes, and having the *T. floridanum* extranuclear genes. The resultant $F_1$ hybrid was then crossed as a female parent with a second maize line as a male parent to produce a second hybrid, referred to as $BC_1$, with a nuclear genome having a full complement of maize chromosomes in combination with Tripsacum chromosomes, while retaining the extranuclear genes from the Tripsacum. $BC_1$ was crossed as a female parent with a third maize line, producing a third hybrid, $BC_2$, having a nuclear genome of maize chromosomes and a variable (reduced) number of Tripsacum chromosomes, with the Tripsacum extranuclear genes. BC2 plants having lowest numbers of Tripsacum chromosomes were selected and crossed with a fourth maize line, producing a fourth hybrid, $BC_3$, all of which retained the Tripsacum extranuclear genes, with further reduced numbers of Tripsacum chromosomes in the nuclear genome. Some members of the $BC_3$ generation possessed no Tripsacum chromosomes, and those individuals were selected and selfed, producing progeny, referred to as $BC_4$, with a nuclear genome having a full complement of maize chromosomes only, with the extranuclear genes of *Tripsacum floridanum*. None of the plants within the $BC_4$ generation were found to possess any Tripsacum chromosomes. Maize plants of the $BC_4$ generation were selfed, producing the $BC_5$ generation, which possessed a nuclear genome of only maize chromosomes with no chromosomes of Tripsacum, and the extranuclear genes of *Tripsacum floridanum*.

The karyotypes of the maize hybrids possessing the *Tripsacum floridanum* extranuclear genes are summarized as follows:

| Hybrid | Tripsacum chromosomes* | maize chromosomes* | % male fertility |
|---|---|---|---|
| $F_1$ | 18 | 10 | 0 |
| $BC_1$ | 18 | 20 | 0 |
| $BC_2$ | 6–18 | 20 | 0 |
| $BC_3$ | 0–6 | 20 | 0 |
| $BC_4$ | 0 | 20 + 1 telo | 100 |
| $BC_5$ | 0 | 20 or 20 + 1 telo | 100 |

*2n

A sample of at least 2,500 seeds from $BC_4$ generation plants comprising a nuclear genome of either 20 or 20+ chromosomes of *Zea mays* with no chromosomes of Tripsacum, and comprising extranuclear genes of *Tripsacum floridanum*, has been deposited under the conditions of the Budapest Treaty with the American Type Culture Collection (10801 University Blvd, Manassas, Va., 20110–2209, USA) on Jan. 29, 1999, and has been assigned deposit accession no. ATCC 203622.

It is understood that the foregoing detailed description is given merely by way of illustration and that modifications and variations may be made therein without departing from the spirit and scope of the invention.

We claim:

1. A maize plant or parts thereof having a nuclear genome comprising *Zea mays* chromosomes with no Tripsacum chromosomes, and having extranuclear genes comprising *Tripsacum floridanum* extranuclear genes; said maize plant produced by a process comprising crossing *Tripsacum floridanum* as a female parent with *Tripsacum dactyloides* as a male parent to produce an interspecific Tripsacum, followed by crossing said interspecific Tripsacum as a female parent with a *Zea mays* line as a male parent to produce an $F_1$ intergeneric plant, followed by crossing said $F_1$ intergeneric plant as a female parent with the same or different *Zea mays* line as a male parent to produce a $BC_1$ plant, followed by crossing of the $BC_1$ plant as a female parent with the same or different *Zea mays* line as a male parent to produce a $BC_2$ plant, followed by successive crossing of the most recently produced BC plant as a female parent with the same or different *Zea mays* line as a male parent.

2. The maize plant of claim 1 wherein said nuclear genome consists essentially of *Zea mays* chromosomes.

3. The maize plant of claim 1 wherein said extranuclear genes consist essentially of *Tripsacum floridanum* extranuclear genes.

4. An ovule of the maize plant of claim 1.

5. A seed produced by crossing a maize plant of claim 1 as a female parent with a fertile *Zea mays* plant as a male parent, said seed having a nuclear genome comprising *Zea mays* chromosomes with no Tripsacum chromosomes, and having extranuclear genes comprising *Tripsacum floridanum* extranuclear genes.

6. A tissue culture of regenerable cells of the maize plant of claim 1, wherein the tissue regenerates plants having a nuclear genome comprising *Zea mays* chromosomes with no Tripsacum chromosomes, and having an extranuclear genome comprising *Tripsacum floridanum* extranuclear genes.

7. The tissue culture of claim 6, wherein said cells are from a tissue selected from the group consisting of leaves, embryos, ovules, roots, root tips, silks, pollen sacks, flowers, kernels, ears, cobs, husks, and stalks.

8. A maize plant regenerated from the tissue culture of claim 6 which has a nuclear genome comprising *Zea mays* chromosomes with no Tripsacum chromosomes, and has an extranuclear genome comprising *Tripsacum floridanum* extranuclear genes.

9. A method for producing a first generation maize seed comprising crossing a maize plant of claim 1 as a female parent with a different parent *Zea mays* plant as a male parent, and harvesting the resultant first generation maize seed.

10. A maize seed produced by the process of claim 9.

11. A maize plant or parts thereof grown from the seed of claim 10 which have a nuclear genome comprising *Zea mays* chromosomes with no Tripsacum chromosomes, and have extranuclear genes from *Tripsacum floridanum*.

12. Maize seed, representative samples thereof having been deposited as ATCC accession number 203622, said maize seed having a nuclear genome consisting essentially of *Zea mays* chromosomes with no Tripsacum chromosomes, and having extranuclear genes consisting essentially of *Tripsacum floridanum* extranuclear genes.

13. A maize plant or parts thereof having a nuclear genome comprising *Zea mays* chromosomes with no Tripsacum chromosomes, and having extranuclear genes comprising *Tripsacum floridanum* extranuclear genes derived from said seed of claim 12.

14. A maize plant or parts thereof grown from said seed of claim 12.

15. A seed produced by crossing a maize plant of claim 14 as a female parent with a male fertile *Zea mays* plant as a male parent, said seed having a nuclear genome comprising *Zea mays* chromosomes with no Tripsacum chromosomes, and having extranuclear genes comprising *Tripsacum floridanum* extranuclear genes.

16. A tissue culture of regenerable cells of the maize plant of claim 14, wherein the tissue regenerates plants having a nuclear genome comprising *Zea mays* chromosomes with no Tripsacum chromosomes, and having an extranuclear genome comprising *Tripsacum floridanum* extranuclear genes.

17. The tissue culture of claim 16, wherein said cells are from a tissue selected from the group consisting of leaves, embryos, ovules, roots, root tips, silks, pollen sacks, flowers, kernels, ears, cobs, husks, and stalks.

18. A maize plant regenerated from the tissue culture of claim 16 which has a nuclear genome comprising *Zea mays* chromosomes with no Tripsacum chromosomes, and has an extranuclear genome comprising *Tripsacum floridanum* extranuclear genes.

19. A method for producing a maize plant comprising crossing a maize plant of claim 14 as a female parent with a different male parent *Zea mays* plant as a male parent, and harvesting the resultant maize seed.

20. A maize seed produced by the process of claim 19.

21. A maize plant or parts thereof grown from the seed of claim 20 which have a nuclear genome comprising *Zea mays* chromosomes with no Tripsacum chromosomes, and have extranuclear genes from *Tripsacum floridanum*.

22. A first seed having a nuclear genome comprising *Zea mays* chromosomes with no Tripsacum chromosomes, and having extranuclear genes comprising *Tripsacum floridanum* extranuclear genes, said first seed produced by the process of crossing a male fertile *Zea mays* plant as a male parent with a second maize plant as a female parent, wherein said second maize plant used as the female parent is selected from the group consisting of a maize plant grown from a second seed deposited as ATCC accession number 203622 and progeny therefrom, said second seed and said progeny having a nuclear genome comprising *Zea mays* chromosomes with no Tripsacum chromosomes, and having extranuclear genes comprising *Tripsacum floridanum* extranuclear genes.

23. A maize plant or parts thereof grown from said first seed of claim 22.

24. A tissue culture of regenerable cells of the maize plant of claim 23, wherein the tissue regenerates plants having a nuclear genome comprising *Zea mays* chromosomes with no Tripsacum chromosomes, and having an extranuclear genome comprising *Tripsacum floridanum* extranuclear genes.

25. A maize seed selected from the group consisting of a first seed deposited as ATCC accession number 203622, and a second seed harvested from progeny of said first seed, said first seed and said second seed having a nuclear genome comprising *Zea mays* chromosomes with no Tripsacum chromosomes, and having extranuclear genes comprising *Tripsacum floridanum* extranuclear genes.

26. A maize plant or parts thereof grown from said first seed of claim 25.

27. A tissue culture of regenerable cells of the maize plant of claim 26, wherein the tissue regenerates plants having a nuclear genome comprising *Zea mays* chromosomes with no Tripsacum chromosomes, and having an extranuclear genome comprising *Tripsacum floridanum* extranuclear genes.

* * * * *